US00RE44800E

(19) United States
(12) Reissued Patent
Hansson

(10) Patent Number: US RE44,800 E
(45) Date of Reissued Patent: Mar. 11, 2014

(54) DENTAL IMPLANT

(75) Inventor: Stig Hansson, Mölndal (SE)

(73) Assignee: Astrazeneca AB, Sodertalje (SE)

(21) Appl. No.: 10/421,962

(22) Filed: Apr. 24, 2003

Related U.S. Patent Documents

Reissue of:

(64) Patent No.: 6,220,860
Issued: Apr. 24, 2001
Appl. No.: 09/355,708
PCT Filed: Jul. 13, 1999
PCT No.: PCT/SE99/01267
§ 371 (c)(1),
(2), (4) Date: Aug. 3, 1999
PCT Pub. No.: WO00/03656
PCT Pub. Date: Jan. 27, 2000

(30) Foreign Application Priority Data

Jul. 17, 1998 (SE) ..... 9802572

(51) Int. Cl.
*A61C 8/00* (2006.01)

(52) U.S. Cl.
USPC ..... 433/173; 433/174

(58) Field of Classification Search
USPC ..... 433/172–176, 201.1; 411/411; 606/264, 606/265, 275, 301, 305, 310, 311, 312
See application file for complete search history.

(56) References Cited

U.S. PATENT DOCUMENTS

| | | | | | |
|---|---|---|---|---|---|
| 4,416,629 | A | * | 11/1983 | Mozsary et al. | 433/174 |
| 4,624,673 | A | | 11/1986 | Meyer | |
| 4,626,214 | A | | 12/1986 | Artal et al. | |
| 4,668,191 | A | * | 5/1987 | Plischka | 433/174 |
| 4,723,913 | A | | 2/1988 | Bergman | |
| 4,744,754 | A | | 5/1988 | Ross | |
| 4,826,434 | A | | 5/1989 | Krueger | |
| 4,842,518 | A | * | 6/1989 | Linkow et al. | 433/174 |
| 4,878,915 | A | * | 11/1989 | Brantigan | 623/17.11 |
| 4,988,299 | A | | 1/1991 | Branemark | 433/174 |
| 5,087,199 | A | | 2/1992 | Lazarof | |
| 5,310,343 | A | * | 5/1994 | Hasegawa et al. | 433/173 |
| 5,435,723 | A | | 7/1995 | O'Brien | |
| 5,527,183 | A | | 6/1996 | O'Brien | 433/174 |
| 5,562,672 | A | * | 10/1996 | Huebner et al. | 606/73 |
| 5,588,838 | A | | 12/1996 | Hansson et al. | |
| 5,601,553 | A | | 2/1997 | Trebing et al. | |
| 5,639,237 | A | * | 6/1997 | Fontenot | 433/173 |
| 5,642,996 | A | | 7/1997 | Mochida et al. | |
| 5,695,336 | A | * | 12/1997 | Lazzara et al. | 433/173 |
| 5,915,967 | A | * | 6/1999 | Clokie | 433/173 |
| 5,931,675 | A | * | 8/1999 | Callan | 433/173 |
| 5,975,903 | A | * | 11/1999 | Shoher et al. | 433/173 |
| 6,045,554 | A | | 4/2000 | Grooms et al. | |
| 6,231,606 | B1 | | 5/2001 | Graf et al. | |

FOREIGN PATENT DOCUMENTS

| | | | |
|---|---|---|---|
| DE | 4130891 | A1 | 3/1992 |
| EP | 0 263 274 | B1 | 4/1988 |
| EP | 0 424 734 | A1 | 5/1991 |
| JP | 3011305 | | 5/1995 |
| JP | 8-510400 | | 11/1996 |
| TW | 239291 | | 1/1995 |
| WO | WO 94/07428 | | 4/1994 |
| WO | 9417750 | | 8/1994 |
| WO | WO-95/17135 | | 6/1995 |
| WO | 9729713 | | 8/1997 |
| WO | WO 97/43976 | A1 | 11/1997 |

* cited by examiner

*Primary Examiner* — Yogesh Patel
(74) *Attorney, Agent, or Firm* — Birch, Stewart, Kolasch & Birch, LLP

(57) ABSTRACT

Dental implant (10) for rotation into the bone tissue of a jaw bone consisting of a body having an axis of rotation, a coronal end surface (5), an apical end surface (1) and a generally cylindrical section (7) which has a coronal edge coincident with, or in close proximity to, the coronal end surface and an outer peripheral surface which extends apically towards the apical end surface from the coronal edge. The outer peripheral surface is presented by a circumferentially-oriented roughness (19) comprising a series of circumferentially-oriented peaks which are axially spaced apart by troughs and oriented at an inclined angle to the axis of rotation. The height from the troughs to the peaks throughout the circumferentially-oriented roughness is greater than 0.2 mm.

24 Claims, 2 Drawing Sheets

New
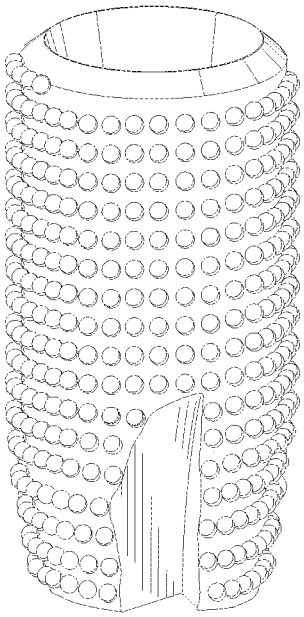
Fig. 5a
New

DENTAL IMPLANT

Matter enclosed in heavy brackets [ ] appears in the original patent but forms no part of this reissue specification; matter printed in italics indicates the additions made by reissue.

FIELD OF THE INVENTION

The present invention relates to a dental implant for rotation into the bone tissue of a jaw bone of a partially or totally edentulous patient consisting of a body which has an axis of rotation and on which is provided a circumferentially-oriented roughness comprising a series of circumferentially-oriented peaks which are axially spaced apart by troughs and angularly inclined to the axis of rotation.

BACKGROUND OF THE INVENTION

Dental implants of this type are for use as the anchoring members of dental prosthesis. To this end, the dental implant is inserted into a bore-hole drilled into the bone tissue of a jaw bone (maxilla or mandible) at a site where the dental prosthesis is required by rotating the dental implant into the bore-hole. The convention in the art is for the circumferentially-oriented roughness on the dental implant to take the form of a screw thread and in this case the bore-hole will typically be (i) provided with internal threads in advance, or (ii) left untapped with the dental implant being provided with a self-tapping capacity, e.g. by the provision of one or more axially-extending cutting recesses or notches in the screw thread.

A superstructure having the prosthetic part of the prosthesis is then secured to the dental implant. The superstructure will typically consist of a spacer or transmucosal component which engages to the dental implant to bridge the gingiva overlying the maxilla or mandible at the dental implant site and the prosthetic part, e.g. a crown, bridge or denture, is then secured to the spacer. There are various other forms that the superstructure can take as is known in the art. For instance, the prosthetic part may be secured directly to the dental implant.

The long-term integrity of the prosthesis is highly dependent on the successful osseointegration of the dental implant with the bone tissue of the maxilla or mandible, that is to say, the remodelling of the bone tissue in the maxilla or mandible into direct apposition with the dental implant. A study on the factors which affect the osseointegration of dental implants was undertaken by Professor Per-Ingvar Branemark and co-workers and the results were published in a book entitled "Osseointegrated Implants in the Treatment of the Edentulous Jaw: Experience from a 10-Year Period", Almqvist & Wiskell International, Stockholm, Sweden, 1977. It was found by Branemark et al that successful osseointegration depends upon inter alia the use of biocompatible materials for the dental implant, for example titanium and alloys thereof, and the surgical procedure adopted, for example leaving the dental implant unloaded for several months before adding the superstructure.

Dental implants having a circumferentially-oriented roughness have some notable advantages in promoting successful osseointegration with the adjacent bone tissue, a major one being as a result of the fact that the main loads on the dental implant in the clinical situation are axial loads. These dental implants are very well suited to support axial loads and this may be particularly important in the initial stages of the osseointegration process in which it is important that the dental implant is fully stable and as immovable as possible in the bore-hole (primary fixation). One can consider this to be due to the bone tissue growing into the troughs between adjacent peaks of the circumferentially-oriented roughness on the dental implant.

In Applicant's prior International patent application publication WO94/07428 there is disclosed a dental implant consisting of a body which has a coronal end surface, an apical end surface and a generally cylindrical section which extends apically from a position in close proximity to the coronal end surface. The outer peripheral surface of the generally cylindrical section is presented by one or more screw threads each of height no more than 0.2 mm, so-called microthreads. The use of microthreads enables the dental implant to be both tapped and screwed into a bore-hole provided in a jaw bone.

It would be an advantage to provide a dental implant with a circumferentially-oriented roughness which commences close to the coronal end surface of the dental implant as in WO94/07428 but which has a trough-to-peak height greater than that of microthreads.

SUMMARY OF THE INVENTION

According to the present invention there is thus provided a dental implant for rotation into the bone tissue of a jaw bone consisting of a body having an axis of rotation, a coronal end surface, an apical end surface and a generally cylindrical section, the generally cylindrical section having a coronal edge coincident with, or in close proximity to, the coronal end surface and an outer peripheral surface which extends apically from the coronal edge towards the apical end surface, the outer peripheral surface being presented by a circumferentially-oriented roughness comprising a series of circumferentially-oriented peaks which are axially spaced apart by troughs and oriented at an inclined angle to the axis of rotation, the height from the troughs to the peaks throughout the circumferentially-oriented roughness being greater than 0.2 mm.

The advantage of providing a dental implant with a circumferentially-oriented roughness which has a height greater than 0.2 mm at, or in close relation to, the coronal end surface of the dental implant is that when the dental implant is implanted in the bone tissue of a jaw bone the bone tissue adjacent the entry point of the dental implant into the jaw bone will interface with the roughness. Axial loading applied to the dental implant by a superstructure mounted thereon will then be transmitted through this bone-roughness interface and counteract bone tissue resorption at the entry point (marginal bone tissue resorption) which can inter alia undermine the stability of a dental implant.

In an embodiment of the invention such as the one hereinafter to be described the coronal edge of the generally cylindrical section is spaced from the coronal end surface of the body by no more than approximately 4% of the distance between the coronal and apical end surfaces of the body. The coronal edge of the generally cylindrical section may be spaced from the coronal end surface of the body by a coronal section of the body having an outer peripheral surface not presented by a circumferentially-oriented roughness. The outer peripheral surface of the coronal section may be smooth or perhaps roughened such as if the implant were grit blasted or etched to produce micropits.

In an embodiment of the invention such as the one hereinafter to be described the height from the troughs to the peaks throughout the circumferentially-oriented roughness is uniform and preferably approximately 0.3 mm.

In an embodiment of the invention such as the one hereinafter to be described each peak has a pair of opposed flank surfaces and the facing flanks of each adjacent pair of peaks are connected by a curved surface.

In an embodiment of the invention such as the one hereinafter to be described the circumferentially-oriented roughness is formed by one or more screw threads. Alternately, the circumferentially-oriented roughness may be formed by a series of axially spaced-apart circumferential lines of beads with the beads in each line optionally being circumferentially spaced-apart.

In an embodiment of the invention such as the one hereinafter to be described the outer peripheral surface of the generally cylindrical section extends apically from the coronal edge over a major proportion of the distance between the coronal edge and the apical end surface of the body.

In an embodiment of the invention such as the one hereinafter to be described the generally cylindrical section has an apical edge which is spaced coronally from the apical end surface of the body by no more than approximately 20% of the distance between the coronal and apical end surfaces of the body and the outer peripheral surface of the generally cylindrical section extends to the apical edge. The apical edge may be spaced from the apical end surface of the body by an apical section of the body having an outer peripheral surface of which at least a coronal portion is presented by a circumferentially-oriented roughness comprising a series of circumferentially-oriented peaks which are axially spaced apart by troughs and oriented at an inclined angle to the axis of rotation, as in the embodiment hereinafter to be described. Alternately, the apical edge may be spaced from the apical end surface of the body by an apical section of the body having an outer peripheral surface not presented by a circumferentially-oriented roughness. The outer peripheral surface of the apical section may be smooth or roughened as for the coronal section.

BRIEF DESCRIPTION OF THE DRAWINGS

By way of example, a self-tapping endosseous screw-type dental implant in accordance with the present invention will now be described with reference to the accompanying Figures of drawings in which:

FIGS. 5a and 5b are perspective views of a second embodiment of the dental implant.*

DESCRIPTION OF EXEMPLARY EMBODIMENT OF THE INVENTION

In the accompanying Figures of drawings there is shown various views of a self-tapping endosseous screw-type dental implant 10 of a dental prosthesis in accordance with the present invention. The implant 10 is for screwing into a bore-hole drilled into a toothless-site in a maxilla or mandible of a partially or fully edentulous patient to anchor to the maxilla or mandible a superstructure of the prosthesis which comprises a prosthetic part, namely one or more artificial teeth. The implant 10 has a circular cross-section and is made from commercially pure titanium, a titanium alloy, another biocompatible metal or metal alloy or a ceramic to promote osseointegration of the implant with the bone tissue of the boundary walls of the bore-hole.

Figure 1:
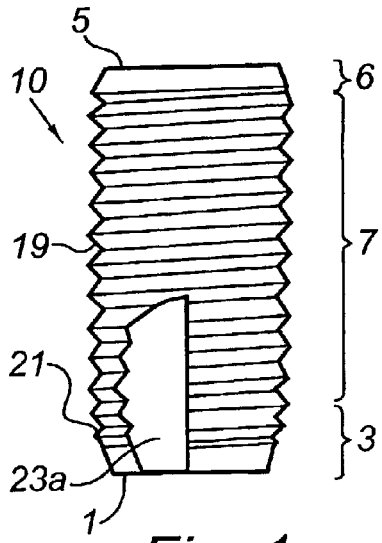
FIG. 1 is a side view of the dental implant.

Referring to FIG. 1, the implant 10 has an apical end 1 which is presented by a first conical section 3 to ease insertion of the implant 10 into the bore-hole, a coronal end 5 presented by a second conical section 6 and a cylindrical intermediate section 7 of constant diameter which extends between the first and second conical sections 3, 6.

Figure 2:
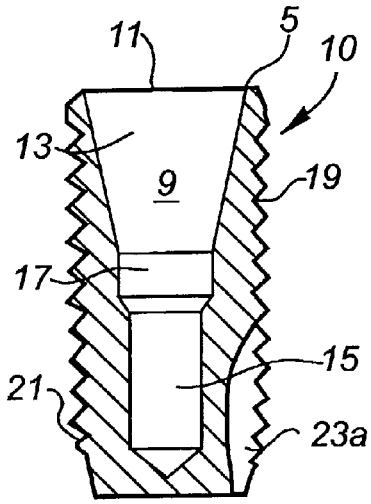
FIG. 2 is a cross-sectional side view of the dental implant.
Figure 3:
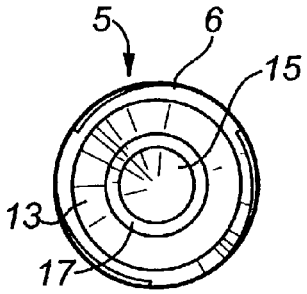
FIG. 3 is a plan view of the dental implant; [and]

The implant 10 has a length in the range 8-19 mm, depending on the clinical situation, and a maximum outer diameter of 3.5 mm or 4.0 mm. The axial extent of the first conical section 3 is no more than 20% of the total length of the implant 10, preferably in the range 7-19% as would be achieved if the first conical section 3 were approximately 1.5 mm in length. The axial extent of the second conical section 6, on the other hand, is no more than 4.0% of the total length of the implant 10, preferably in the range 1.5%-3.8% as would be achieved if the second conical section 6 had an axial extent of approximately 0.3 mm:

Turning to FIGS. 2 and 3, a socket 9 having an open end 11 in the coronal end 5 extends apically into the implant 10. The socket 9 is for receiving an abutment structure (not shown) which will bridge the gingiva overlying the bore-hole and support/present the prosthetic part. The socket 9 consists of a conical coronal section 13, an internally-threaded apical section 15 and a cylindrical intermediate section 17. The abutment structure will have an apical section which is able to be screw retained in the implant socket 9 for releasably securing the abutment structure to the implant 10.

As shown in FIGS. 1 and 2, the implant 10 has a screw thread profile 19 on the cylindrical intermediate section 7 and a screw thread profile 21 on a coronal portion of the first conical section 3. The screw thread profiles 19, 21 are formed by a so-called triple screw thread which extends apically from the junction between the second conical section 6 and the cylindrical intermediate section 7, as will be gathered from FIG. 3 which shows the start of the three individual screw threads which, incidentally, each have the same pitch.

The height of the screw threads over the cylindrical intermediate section 7 is greater than 0.2 mm, preferably 0.3 mm. The height of the screw threads over the first conical section 3 may, on the other hand, be less than 0.2 mm by virtue of the inwardly tapering nature of the first conical section 3. The three screw threads are arranged on the implant 10 such that the juxtaposed coronal and apical flanks of adjacent screw threads are connected by a curved surface, that is to say, there is no axial straight part in-between the adjacent screw threads.

As can also be seen from FIGS. 1 and 2, the tips of the screw threads over the cylindrical intermediate section 7 all lie on a common plane which is parallel to the main axis of the implant 10 when viewed in side section and thus circumscribe the circumference of the cylindrical intermediate section 7. This gives the cylindrical intermediate section 7 its constant diameter.

Figure 4:
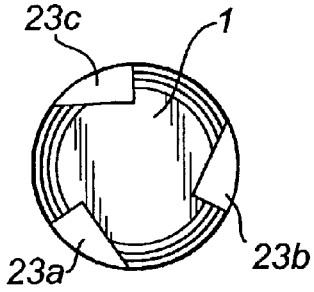
FIG. 4 is an underneath view of the dental implant[.]*.

As shown in FIGS. 1, 2 and 4, the implant 10 has three cutting recesses or grooves 23a, 23b, 23c positioned symmetrically about the circumference of the apical end 1 of the implant 10 for self-tapping of the implant 10 when being screwed into the bore-hole.

Figure 5B:
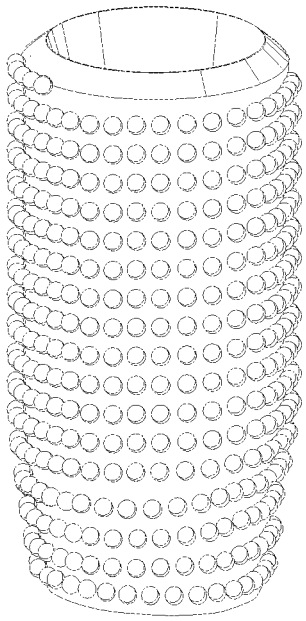

*FIGS. 5a and 5b show a second embodiment of the dental implant. In this arrangement, the circumferentially-oriented roughness may be formed by a series of axially spaced-apart circumferential lines of beads. The beads in each line are optionally circumferentially spaced apart.*

In use, the implant 10 is screwed about its main axis into the bore-hole provided at the toothless-site in the maxilla or mandible such that the coronal and apical threaded sections 19, 21 are embedded in bone tissue with the second conical section 6 protruding from the maxilla or mandible. As the screw threads commence from a position proximate the coronal end 5 of the implant 10, the loads transferred thereby help alleviate the problem of bone tissue resorption at the coronal surface of the maxilla or mandible (marginal bone tissue resorption).

It will be appreciated that the invention has been illustrated with reference to an exemplary embodiment and that the invention can be varied in many different ways within the scope of the appended claims. For instance, individual features of the exemplary embodiment may have equal application in other embodiments of the invention either in isolation or combination with other features of the exemplary embodiment.

Finally, it is to be noted that the inclusion in the appended claims of some of the reference numerals used in the Figures of drawings is purely for illustrative purposes and not to be construed as having a limiting effect on the scope of the claims.

What is claimed is:

1. A dental implant for rotation into the bone tissue of a jaw bone consisting of a body having:

(a) an axis of rotation;

(b) a coronal end surface;

(c) an apical end surface; and (d) a generally cylindrical section which has:

(i) a coronal edge in close proximity to[.] the coronal end surface, and (ii) an outer peripheral surface which extends apically[,] towards the apical end surface from the coronal edge and is presented by a circumferentially-oriented roughness comprising a series of circumferentially-oriented peaks which are axially spaced apart by troughs and oriented at [an] *a generally constant* inclined angle *with respect* to the axis of rotation *so the dental implant rotates and screws into the jaw bone*;

wherein the height from the troughs to the peaks throughout the circumferentially-oriented roughness is greater than 0.2 mm, and the coronal edge of the generally cylindrical section [is] *separates the generally cylindrical section from a conical portion extending to the coronal edge, the conical portion tapering inwardly as the conical portion extends from the coronal edge to the coronal end surface, the coronal edge and circumferentially-oriented roughness are* spaced from the coronal end surface of the body by no more than [approximately] 4% of the distance between the coronal and apical end surfaces of the [body.] *body,*

*wherein the largest diameter of the dental implant is at the generally cylindrical section.*

2. The implant as claimed in claim 1, wherein [the coronal edge of the generally cylindrical section is spaced from the coronal end surface of the body by a coronal section of the body having] *the conical portion has* an outer peripheral surface not presented by a circumferentially-oriented roughness.

3. The implant as claimed in claim 1, wherein the height from the troughs to the peaks throughout the circumferentially-oriented roughness is [approximately] 0.3 mm.

4. The implant as claimed in claim 1, wherein the circumferentially-oriented roughness is formed by one or more screw threads.

5. The implant as claimed in claim 1, wherein the circumferentially-oriented roughness is formed by a series of axially spaced-apart circumferential lines of beads.

6. The implant as claimed in claim 5, wherein the beads in each line are circumferentially spaced-apart.

7. The implant as claimed in claim 1, wherein the outer peripheral surface of the generally cylindrical section extends apically from the coronal edge over a major proportion of the distance between the coronal edge and the apical end surface of the body.

8. The implant as claimed in claim 1, wherein the generally cylindrical section has an apical edge which is spaced from the apical end surface of the body by no more than [approximately] 20% of the distance between the coronal and apical end surfaces of the body and the outer peripheral surface of the generally cylindrical section extends to the apical edge.

[9. A dental implant for rotation into the bone tissue of a jaw bone consisting of a body having:

(a) an axis of rotation;

(b) a coronal end surface;

(c) an apical end surface; and (d) a generally cylindrical section which has:

(i) a coronal edge coincident with the coronal end surface, and (ii) an outer peripheral surface which extends apically towards the apical end surface from the coronal edge and is presented by a circumferentially-oriented roughness comprising a series of circumferentially-oriented peaks which are axially spaced apart by troughs and oriented at an inclined angle to the axis of rotation;

wherein the height from the troughs to the peaks throughout the circumferentially-oriented roughness is greater than 0.2 mm.]

[10. The implant as claimed in claim 9, wherein the height from the troughs to the peaks throughout the circumferentially-oriented roughness is approximately 0.3 mm.]

[11. The implant as claimed in claim 9, wherein the circumferentially-oriented roughness is formed by one or more screw threads.]

[12. The implant as claimed in claim 9, wherein the circumferentially-oriented roughness is formed by a series of axially spaced-apart circumferential lines of beads.]

[13. The implant as claimed in claim 12, wherein the beads in each line are circumferentially spaced-apart.]

[14. The implant as claimed in claim 9, wherein the outer peripheral surface of the generally cylindrical section extends apically from the coronal edge over a major proportion of the distance between the coronal edge and the apical end surface of the body.]

[15. The implant as claimed in claim 9, wherein the generally cylindrical section has an apical edge which is spaced from the apical end surface of the body by no more than approximately 20% of the distance between the coronal and apical end surfaces of the body and the outer peripheral surface of the generally cylindrical section extends to the apical edge.]

*16. The implant as claimed in claim 1, wherein the coronal edge of the generally cylindrical section is spaced from the coronal end surface of the body by a coronal section of the body having an outer peripheral surface not presented by the circumferentially-oriented roughness that is no more than 4% of the distance between the coronal and apical end surfaces of the body.*

*17. The implant as claimed in claim 1, wherein the height from the troughs to the peaks throughout the circumferentially-oriented roughness is substantially constant.*

*18. The implant as claimed in claim 1, wherein in an implanted state, the coronal edge of the dental implant protrudes from a maxilla or mandible so as to receive an artificial tooth.*

*19. A dental implant for rotation into the bone tissue of a jaw bone comprising a body having:*

*(a) an axis of rotation;*

*(b) a coronal end surface;*

*(c) an apical end surface; and*

*(d) a section which has:*

*i. a coronal edge in close proximity to the coronal end surface, and*

*ii. an outer peripheral surface which extends apically towards the apical end surface from the coronal edge and is presented by a circumferentially-oriented roughness comprising a series of circumferentially-oriented peaks which are axially spaced apart by troughs and oriented at a generally constant inclined angle to the axis of rotation so the dental implant rotates and screws into the jaw bone;*

*wherein the height from the troughs to the peaks throughout the circumferentially-oriented roughness is greater than 0.2 mm, and the coronal edge of the section separates the section from a conical portion extending to the coronal edge, the conical portion tapering inwardly as the conical portion extends form the coronal edge to the coronal end surface, the coronal edge and circumferentially-oriented roughness are spaced from the coronal end surface of the body by the conical portion of the body having an outer peripheral surface not presented by the circumferentially-oriented roughness that is no more than 4% of the distance between the coronal and apical end surfaces of the body,*

*wherein the largest diameter of the dental implant is at the circumferentially-oriented roughness.*

*20. The implant as claimed in claim 19, wherein the height from the troughs to the peaks throughout the circumferentially-oriented roughness is 0.3 mm.*

*21. The implant as claimed in claim 19, wherein the circumferentially-oriented roughness is formed by one or more screw threads.*

*22. The implant as claimed in claim 19, wherein the circumferentially-oriented roughness is formed by a series of axially spaced-apart circumferential lines of beads.*

*23. The implant as claimed in claim 22, wherein the beads in each line are circumferentially spaced-apart.*

*24. The implant as claimed in claim 19, wherein the outer peripheral surface of the cylindrical section extends apically from the coronal edge over a major portion of the distance between the coronal edge and the apical end surface of the body.*

*25. The implant as claimed in claim 19, wherein the cylindrical section has an apical edge which is spaced from the apical end surface of the body by no more than 20% of the distance between the coronal and apical end surfaces of the body and the outer peripheral surface of the cylindrical section extends to the apical edge.*

*26. The implant as claimed in claim 19, wherein a spacer or transmucosal component is engaged to the dental implant.*

*27. The implant as claimed in claim 19, wherein the height from the troughs to the peaks throughout the circumferentially-oriented roughness is substantially constant.*

*28. The implant as claimed in claim 19, wherein in an implanted state, the coronal edge of the dental implant protrudes from a maxilla or mandible so as to receive an artificial tooth.*

*29. A dental implant for implanting in a jaw bone into a bore-hole from an entry point thereof, said implant comprising a body having:*

*(a) an axis of rotation;*

*(b) a coronal end surface;*

*(c) an apical end surface; and*

*(d) a section which has:*

*i. a coronal edge in close proximity to the coronal end surface, and*

*ii. an outer peripheral surface which extends apically towards the apical end surface from the coronal edge and is presented by a circumferentially-oriented roughness comprising a series of circumferentially-oriented peaks which are axially spaced apart by troughs and oriented at a generally constant inclined angle to the axis of rotation so the dental implant rotates and screws into the jaw bone;*

*wherein the height from the troughs to the peaks throughout the circumferentially-oriented roughness of the cylindrical section is greater than 0.2 mm, and the coronal edge of the cylindrical section separates the cylindrical section from a conical portion extending to the coronal edge, the conical portion tapering inwardly as the conical portion extends from the coronal edge to the coronal end surface, the coronal edge and circumferentially-oriented roughness are spaced from the coronal end surface of the body by the conical portion of the body having an outer peripheral surface not presented by the circumferentially-oriented roughness that is no more than 4% of the distance between the coronal and apical end surfaces of the body, and*

*wherein in an implanted state, said circumferentially-oriented roughness of the section adapted to interface with the bone tissue adjacent said entry point of the dental implant,*

*wherein the largest diameter of the dental implant is at the circumferentially-oriented roughness.*

*30. The implant as claimed in claim 29, wherein the height from the troughs to the peaks throughout the circumferentially-oriented roughness is substantially constant.*

*31. The implant as claimed in claim 29, wherein in the implanted state, the coronal edge of the dental implant protrudes from a maxilla or mandible so as to receive an artificial tooth.*

* * * * *